United States Patent [19]

Kijima et al.

[11] 4,169,157
[45] Sep. 25, 1979

[54] THERAPEUTIC PREPARATIONS FOR PEPTIC ULCERS COMPRISING ALIPHATIC KETONE DERIVATIVE

[75] Inventors: Shizumasa Kijima, Tokyo; Isao Yamatsu, Kawaguchi; Yuichi Inai, Tokyo; Toshiharu Ohgoh, Kohnan; Manabu Murakami, Gifu, all of Japan

[73] Assignee: Eisai Co., Ltd., Tokyo, Japan

[21] Appl. No.: 908,634

[22] Filed: May 23, 1978

[30] Foreign Application Priority Data

May 26, 1977 [JP] Japan .................. 52-60427

[51] Int. Cl.² .............. A61K 31/12; A61K 31/11
[52] U.S. Cl. ................................ 424/331; 424/333
[58] Field of Search ........................... 424/331, 333

[56] References Cited
U.S. PATENT DOCUMENTS

| | | | |
|---|---|---|---|
| 3,729,486 | 4/1973 | Siddall | 424/333 |
| 3,801,652 | 4/1974 | Ruegg | 424/331 |
| 3,824,319 | 7/1974 | Schwartz et al. | 424/331 |
| 3,978,230 | 8/1976 | Schwartz et al. | 424/331 |

*Primary Examiner*—Frederick E. Waddell
*Attorney, Agent, or Firm*—Wenderoth, Lind & Ponack

[57] ABSTRACT

A therapeutic preparation having excellent effect for peptic ulcers with low toxicity which comprises aliphatic ketone derivative of the general formula:

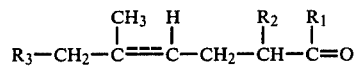

wherein $\rightleftharpoons$ represents a saturated or unsaturated bond, $R_1$ is hydrogen or a lower alkyl group, $R_2$ is hydrogen atom, a lower alkyl group or a lower alkylcarbonyl group, $R_3$ is an aliphatic hydrocarbon group of the general formula:

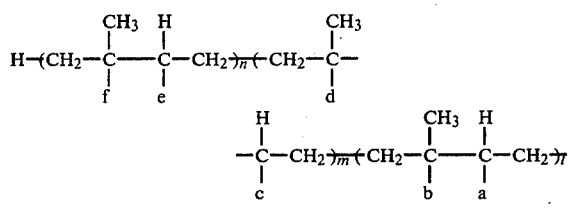

wherein l, m and n are 0 or 1, provided that $l+m+n \geq 2$; and a, b, c, d, e and f are hydrogen atom, or they may form a bond of a—b, c—d or e—f, provided that if the bond $\rightleftharpoons$ is a saturated bond, the a, b, c, d, e and f represent all hydrogen atom.

2 Claims, No Drawings

THERAPEUTIC PREPARATIONS FOR PEPTIC ULCERS COMPRISING ALIPHATIC KETONE DERIVATIVE

This invention relates to a therapeutic preparation for peptic ulcers, such as gastric ulcer, duodenal ulcer and the like, which comprises an aliphatic ketone compound represented by the general formula:

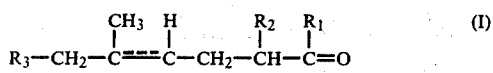

wherein $=$ represents a saturated or unsaturated bond, $R_1$ is hydrogen or a lower alkyl group, $R_2$ is hydrogen, a lower alkyl group or a lower alkylcarbonyl group, $R_3$ is an aliphatic hydrocarbon group of the formula:

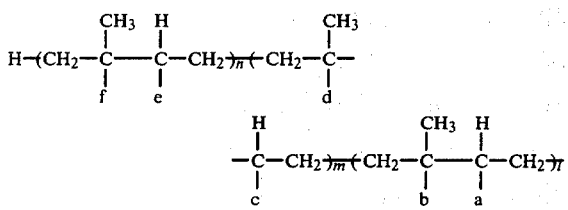

wherein l, m and n are 0 or 1, provided that $l+m+n \geq 2$; and a, b, c, d, e and f represent hydrogen atom, or they may form a bond of a—b, c—d and e—f, provided that when the bond$=$is an unsaturated bond, a, b, c, d, e and f are all hydrogen atoms.

The fundamental medicine therapy for the treatment of the peptic ulcers comprises generally decreasing so-called attacking factor (hydrochloric acid, pepsin) to the mucosal membrane of digestic tract, and increasing the protecting factor (resistance of mucosal membrane and surgical reparative force) to the attacking factor.

Typical medicines used for decreasing the attacking factor include antacids, such as sodium bicarbonate, magnesium tri-silicate, synthetic aluminum silicate and the like; parasympathicolytics, such as propantheline bromide, buscopan and the like. These medicines, however, have the following drawbacks. Although the antacids have effects which relieve dramatically subjective sympton such as abdominal pain, nausea, such effects are transient.

In addition, the acidity of the gastric juice is rather increased due to the acid rebound phenomenon by using the above-mentioned antacid. This makes the symptons rather worse. The parasympathicolytics are effectively used for decreasing the secretion of the gastric juice, to depress the attacking factor. However, the use of para-sympathicolytics is contraindicated to patients accompanied with glaucoma, hypertrophy of the prostate, heart disease, ileus or obstruction of the neck of the bladder, because they are accompanied with the side effects such as disturbance of vision, thirst, dysuria, constipation. Their use is therefore considerably restricted.

Illustrative medicine having anti-pepsine effect is salazo sulfapyridine which is said to have an effect of increasing the protecting factor. However, this medicine is not so effective for treatment of peptic ulcers. In addition, the medicine is contraindicated to the patients sensitive to sulfa-drug, and it may be accompanied with the side effects such as nausea, anorexis, leukopenia and the like.

It can be generally said that the therapy using the medicine which decreases the attacking factor is so-called symptomatic therapy. On the other hand, it can be said that the therapy using the medicine which increases the protecting factor (resistance of mucosal membrane of digestive tract) is so-called causal therapy, since it is directed to recover positively the surgical injury on the mucous membrane of the digestive tract as the results of increasing the protecting factor of said membrane (resistance of mucosal membrane) against the attacking factor and of accelerating a regenerating action of said injured membrane.

In a recent medicine therapy for the peptic ulcers, the peptic ulcer is fundamentally treated by administering a medicine which increases the protecting factor while relieving a subjective symptom by the use of a medicine which decreases the attacking factor. There have been previously used chlorophylline preparations such as sodium copperchlorophylline and the like as the medicine for increasing the protecting factor. Study has been, however, carried out to pursue a medicine having effect on intensifying the regeneration of injured digestive tract. The preparation of geranylfarnesyl acetate (generally called as gefarnate) was thus developed; and the pursuit was achieved in the first place. In spite of said development, there has been further pursued a medicine having more improved effect.

We researched same compounds for using the treatment of peptic ulcers, which have more improved effect than that of the gefarnate in regard to regeneration of injured mucous membrane, and found the compounds according to this invention.

The aliphatic ketone derivatives of the formula (I) to be used to accomplish the object of this invention include the known compounds and novel compounds. Examples of the known compounds are as follows:

6,10,14-trimethyl-5,9,13-pentadecatriene-2-on
6,10,14-trimethyl-5,9-pentadecadiene-2-on
6,10,14-trimethyl-5-pentadecaene-2-on
6,10,14-trimethyl-pentadecane-2-on
7,11,15-trimethyl-hexadecane-3-on
8,12,16-trimethyl-heptadecane-4-on
8,12,16-trimethyl-7-heptadecaene-4-on
2,7,11,15-tetramethyl-6-hexadecaene-3-on
6,10,14,18-tetramethyl-5,9,13,17-nonadecatetraene-2-on
6,10,14,18-tetramethyl-5-nonadecaene-2-on
6,10,14,18-tetramethyl-nonadecane-2-on
7,11,15,19-tetramethyl-6-eicosaene-3-on Examples of the novel compounds are listed in the following tables.

TABLE $$H-(CH_2-\underset{f}{\overset{CH_3}{C}}-\underset{e}{\overset{H}{C}}-CH_2)_n-(CH_2-\underset{d}{\overset{CH_3}{C}}-\underset{c}{\overset{H}{C}}-CH_2)_m-(CH_2-\underset{b}{\overset{CH_3}{C}}-\underset{a}{\overset{H}{C}}-CH_2)_l-CH_2-\overset{CH_3}{\underset{}{C}}-\overset{H}{\underset{}{C}}-CH_2-\overset{R_2}{\underset{}{CH}}-\overset{R_1}{\underset{}{C}}=O \quad (1)$$

| No. | l | m | n | a | b | c | d | e | f | R₁ | R₂ | — | Molecular Formula | Elementary Analysis (%) C | H | MAS (M⁺) |
|---|---|---|---|---|---|---|---|---|---|---|---|---|---|---|---|---|
| 1 | 1 | 1 | 0 | H | H | — | | | | CH₃ | H | Δ | C₁₈H₃₂O | Calculated: 81.75 Found: 81.62 | 12.20 12.31 | 264 |
| 2 | 1 | 1 | 0 | — | | — | | | | CH₃ | —COCH₃ | Δ | C₂₀H₃₂O₂ | Calculated: 78.89 Found: 78.91 | 10.59 10.52 | 304 |
| 3 | 1 | 1 | 0 | — | | H | H | | | CH₃ | —COCH₃ | Δ | C₂₀H₃₄O₂ | Calculated: 78.38 Found: 78.21 | 11.18 11.10 | 306 |
| 4 | 1 | 1 | 0 | H | H | H | H | | | CH₃ | —COCH₃ | Δ | C₂₀H₃₆O₂ | Calculated: 77.86 Found: 77.69 | 11.76 11.71 | 308 |
| 5 | 1 | 1 | 0 | H | H | H | H | | | CH₃ | —COCH₃ | HH | C₂₀H₃₈O₂ | Calculated: 77.36 Found: 77.29 | 12.34 12.27 | 310 |
| 6 | 1 | 1 | 0 | H | H | | — | | | CH₃ | —COCH₃ | Δ | C₂₀H₃₄O₂ | Calculated: 78.38 Found: 78.30 | 11.18 11.22 | 306 |
| 7 | 1 | 1 | 0 | — | | | — | | | CH₃ | CH₃ | Δ | C₁₉H₃₂O | Calculated: 82.54 Found: 82.41 | 11.66 11.51 | 276 |
| 8 | 1 | 1 | 0 | H | H | | — | | | CH₃ | CH₃ | Δ | C₁₉H₃₄O | Calculated: 81.95 Found: 81.68 | 12.31 12.19 | 278 |
| 9 | 1 | 1 | 0 | — | | H | H | | | CH₃ | CH₃ | Δ | C₁₉H₃₄O | Calculated: 81.95 Found: 81.79 | 12.31 12.40 | 278 |
| 10 | 1 | 1 | 0 | H | H | H | H | | | CH₃ | CH₃ | Δ | C₁₉H₃₆O | Calculated: 81.36 Found: 81.51 | 12.94 13.02 | 280 |
| 11 | 1 | 1 | 0 | H | H | H | H | | | CH₃ | CH₃ | HH | C₁₉H₃₈O | Calculated: 80.78 Found: 80.71 | 13.56 13.48 | 282 |
| 12 | 1 | 1 | 0 | — | | | — | | | H | C₂H₅ | Δ | C₁₉H₃₂O | Calculated: 82.54 Found: 82.51 | 11.66 11.62 | 276 |
| 13 | 1 | 1 | 0 | — | | H | H | | | H | C₂H₅ | Δ | C₁₉H₃₄O | Calculated: 81.95 Found: 81.80 | 12.31 12.19 | 278 |
| 14 | 1 | 1 | 0 | H | H | | — | | | H | C₂H₅ | Δ | C₁₉H₃₄O | Calculated: 81.95 Found: 81.72 | 12.31 12.22 | 278 |
| 15 | 1 | 1 | 0 | H | H | H | H | | | H | C₂H₅ | Δ | C₁₉H₃₆O | Calculated: 81.36 Found: 81.20 | 12.94 13.01 | 280 |
| 16 | 1 | 1 | 0 | — | | | — | | | H | n-C₃H₇ | Δ | C₂₀H₃₄O | Calculated: 82.69 Found: 82.81 | 11.80 11.62 | 290 |
| 17 | 1 | 1 | 0 | H | H | | — | | | H | n-C₃H₇ | Δ | C₂₀H₃₆O | Calculated: 82.12 Found: 82.16 | 12.40 12.51 | 292 |
| 18 | 1 | 1 | 0 | — | | H | H | | | H | n-C₃H₇ | Δ | C₂₀H₃₆O | Calculated: 82.12 Found: 82.31 | 12.40 12.29 | 292 |
| 19 | 1 | 1 | 0 | — | | | — | | | H | i-C₃H₇ | Δ | C₂₀H₃₄O | Calculated: 82.69 Found: 82.76 | 11.80 11.69 | 290 |
| 20 | 1 | 1 | 0 | H | H | | — | | | H | i-C₃H₇ | Δ | C₂₀H₃₆O | Calculated: 82.12 Found: 81.96 | 12.40 12.52 | 292 |
| 21 | 1 | 1 | 0 | — | | H | H | | | H | i-C₃H₇ | Δ | C₂₀H₃₆O | Calculated: 82.12 Found: 82.31 | 12.40 12.31 | 292 |
| 22 | 1 | 1 | 0 | H | H | H | H | | | H | i-C₃H₇ | HH | C₂₀H₄₀O | Calculated: 81.10 Found: 81.19 | 13.60 13.49 | 296 |
| 23 | 1 | 1 | 1 | — | | H | H | — | | CH₃ | H | Δ | C₂₃H₄₀O | Calculated: 83.06 Found: 82.96 | 12.13 12.26 | 332 |
| 24 | 1 | 1 | 1 | — | | | — | | | CH₃ | H | Δ | C₂₃H₄₀O | Calculated: 83.06 Found: 83.18 | 12.13 12.07 | 332 |
| 25 | 1 | 1 | 1 | — | | H | H H | | H | CH₃ | H | Δ | C₂₃H₄₂O | Calculated: 82.56 Found: 82.39 | 12.65 12.55 | 334 |
| 26 | 1 | 1 | 1 | — | | | — | | | CH₃ | COCH₃ | Δ | C₂₅H₄₀O₂ | Calculated: 80.59 Found: 80.34 | 10.82 10.91 | 372 |
| 27 | 1 | 1 | 1 | — | | H | H | — | | CH₃ | COCH₃ | Δ | C₂₅H₄₂O₂ | Calculated: 80.15 Found: 80.06 | 11.30 11.46 | 374 |
| 28 | 1 | 1 | 1 | — | | | H | | H | CH₃ | COCH₃ | Δ | C₂₅H₄₂O₂ | Calculated: 80.15 Found: 80.42 | 11.30 11.17 | 374 |
| 29 | 1 | 1 | 1 | — | | H | H H | H | H | CH₃ | COCH₃ | Δ | C₂₅H₄₄O₂ | Calculated: 79.73 Found: 79.68 | 11.78 11.57 | 376 |
| 30 | 1 | 1 | 1 | H | H | H | H | H | H | CH₃ | COCH₃ | Δ | C₂₅H₄₆O₂ | Calculated: 79.30 Found: 79.56 | 12.25 12.19 | 378 |
| 31 | 1 | 1 | 1 | H | H | H | H | H | H | CH₃ | COCH₃ | HH | C₂₅H₄₈O₂ | Calculated: 78.88 Found: 78.72 | 12.71 12.65 | 380 |
| 32 | 1 | 1 | 1 | — | | | — | | | CH₃ | CH₃ | Δ | C₂₄H₄₀O | Calculated: 83.65 Found: 83.51 | 11.70 11.58 | 344 |
| 33 | 1 | 1 | 1 | — | | H | H | — | | CH₃ | CH₃ | Δ | C₂₄H₄₂O | Calculated: 83.17 Found: 83.24 | 12.22 12.19 | 346 |
| 34 | 1 | 1 | 1 | — | | | H | | H | CH₃ | CH₃ | Δ | C₂₄H₄₂O | Calculated: 83.17 Found: 82.98 | 12.22 12.31 | 346 |
| 35 | 1 | 1 | 1 | — | | H | H | H | H | CH₃ | CH₃ | Δ | C₂₄H₄₄O | Calculated: 82.69 Found: 82.51 | 12.72 12.86 | 348 |
| 36 | 1 | 1 | 1 | H | H | H | H | H | H | CH₃ | CH₃ | Δ | C₂₄H₄₆O | Calculated: 82.21 Found: 82.12 | 13.23 13.33 | 350 |
| 37 | 1 | 1 | 1 | H | H | H | H | H | H | CH₃ | CH₃ | HH | C₂₄H₄₈O | Calculated: 81.74 | 13.72 | 352 |

TABLE-continued

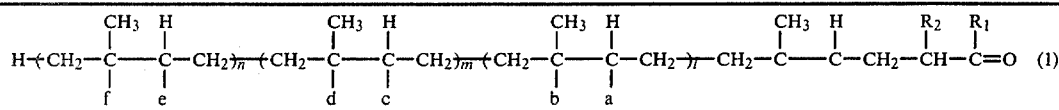

| No. | l | m | n | a | b | c | d | e | f | R₁ | R₂ | === | Molecular Formula | Elementary Analysis (%) | | MAS (M⁺) |
|---|---|---|---|---|---|---|---|---|---|---|---|---|---|---|---|---|
| | | | | | | | | | | | | | | C | H | |
| 38 | 1 | 1 | 1 | — | | — | | — | | C₂H₅ | H | Δ | C₂₄H₄₀O | Calculated: 83.65  Found: 83.91 | 11.70  11.58 | 344 |
| | | | | | | | | | | | | | | Found: 81.82 | 13.66 | |
| 39 | 1 | 1 | 1 | — | | H | H | — | | C₂H₅ | H | Δ | C₂₄H₄₂O | Calculated: 83.17  Found: 83.12 | 12.22  12.19 | 346 |
| 40 | 1 | 1 | 1 | — | | — | H | H | | C₂H₅ | H | Δ | C₂₄H₄₂O | Calculated: 83.17  Found: 82.98 | 12.22  12.33 | 346 |
| 41 | 1 | 1 | 1 | — | | H | H | H | H | C₂H₅ | H | Δ | C₂₄H₄₄O | Calculated: 82.69  Found: 82.71 | 12.72  12.59 | 348 |
| 42 | 1 | 1 | 1 | H | H | H | H | H | H | C₂H₅ | H | HH | C₂₄H₄₈O | Calculated: 81.74  Found: 81.61 | 13.72  13.81 | 352 |
| 43 | 1 | 1 | 1 | — | | — | | — | | n-C₃H₇ | H | Δ | C₂₅H₄₂O | Calculated: 83.73  Found: 83.59 | 11.81  11.77 | 358 |
| 44 | 1 | 1 | 1 | — | | H | H | — | | n-C₃H₇ | H | Δ | C₂₅H₄₄O | Calculated: 83.26  Found: 83.32 | 12.30  12.30 | 360 |
| 45 | 1 | 1 | 1 | — | | — | H | H | | n-C₃H₇ | H | Δ | C₂₅H₄₄O | Calculated: 83.26  Found: 83.32 | 12.30  12.26 | 360 |
| 46 | 1 | 1 | 1 | — | | H | H | H | H | n-C₃H₇ | H | Δ | C₂₅H₄₆O | Calculated: 82.80  Found: 82.98 | 12.79  12.68 | 362 |
| 47 | 1 | 1 | 1 | H | H | H | H | H | H | n-C₃H₇ | H | Δ | C₂₅H₄₈O | Calculated: 82.34  Found: 82.55 | 13.27  13.17 | 364 |
| 48 | 1 | 1 | 1 | H | H | H | H | H | H | n-C₃H₇ | H | HH | C₂₅H₅₀O | Calculated: 81.89  Found: 81.96 | 13.75  13.53 | 366 |
| 49 | 1 | 1 | 1 | — | | — | | — | | i-C₃H₇ | H | Δ | C₂₅H₄₂O | Calculated: 83.73  Found: 83.63 | 11.81  11.92 | 358 |
| 50 | 1 | 1 | 1 | — | | H | H | — | | i-C₃H₇ | H | Δ | C₂₅H₄₄O | Calculated: 83.26  Found: 83.43 | 12.30  12.35 | 360 |
| 51 | 1 | 1 | 1 | — | | — | H | H | | i-C₃H₇ | H | Δ | C₂₅H₄₄O | Calculated: 83.26  Found: 82.99 | 12.30  12.47 | 360 |
| 52 | 1 | 1 | 1 | — | | H | H | H | H | i-C₃H₇ | H | Δ | C₂₅H₄₆O | Calculated: 82.80  Found: 82.92 | 12.79  12.86 | 362 |
| 53 | 1 | 1 | 1 | H | H | H | H | H | H | i-C₃H₇ | H | Δ | C₂₅H₄₈O | Calculated: 82.34  Found: 82.19 | 13.27  13.31 | 364 |
| 54 | 1 | 1 | 1 | H | H | H | H | H | H | i-C₃H₇ | H | HH | C₂₅H₅₀O | Calculated: 81.89  Found: 81.84 | 13.75  13.71 | 366 |

These novel compounds can be synthesized by various methods depending upon their chemical structures. The following is one of examples of the methods. The compounds of the Formula (I), wherein $R_1$ is hydrogen or a lower alkyl group and $R_2$ is hydrogen atom or a lower alkyl group (the compound Nos. 1, 7-25, 32-54 in the Tables) can be prepared as shown in the following chemical equation, by reacting the aliphatic halide (II) with ethyl acetoacetate derivative (III) in the presence of a condensation agent such as metallic sodium, metallic potassium, sodium ethylate, sodium hydrate and the like, and using, if required, a solvent such as ethanol, t-butanol, dioxane, benzen, and the like, to perform a condensation reaction. The resulting condensation product (IV) is treated, usually without isolation, with an alkali reagent, such as an aqueous dilute sodium hydroxide solution, aqueous dilute potassium hydroxide solution and the like, to allow the ester cleavage tne the decarboxylation.

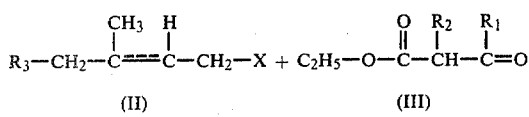

i) ester cleavage
ii) decarboxylation → (I)

wherein $R_1$ is hydrogen or a lower alkyl group, $R_2$ is hydrogen atom or a lower alkyl group, X is a halogen atom, and $R_3$ and == have the same meanings as defined above.

The compound of the Formula I, wherein $R_1$ is a lower alkyl group, and $R_2$ is a lower alkylcarbonyl group (the compound Nos. 2-6, 26-31) can be prepared as shown in the following chemical equation, by reacting aliphatic halide (II) with ketone compound (IV) in the presence of a condensation agent such as metallic sodium, metallic potassium, sodium ethylate, sodium hydrate and the like, and using, if required, a solvent such as ethanol, t-butanol, dioxane, benzen and the like.

$$\underset{(II)}{R_3-CH_2-\overset{CH_3}{\underset{|}{C}}=\overset{H}{\underset{|}{C}}-CH_2-X} + \underset{(V)}{R_2-CH_2-\overset{R_1}{\underset{|}{C}}=O}$$

$$\xrightarrow{\text{condensation}} (I)$$

wherein $R_1$ is a lower alkyl group, $R_2$ is a lower alkylcarbonyl group, and $R_3$, X and == have the same meanings as stated before.

The compounds of the Formula (I), wherein the bond == is an unsaturated bond and $R_3$ is $$H\text{-}(CH_2-\overset{CH_3}{\underset{|}{CH}}-CH_2-CH_2)_n\text{-}(CH_2-\overset{CH_3}{\underset{|}{CH}}-CH_2-CH_2)_m\text{-}(CH_2-\overset{CH_3}{\underset{|}{CH}}-CH_2-CH_2)_l\text{-}$$

wherein l, m and n have the same meanings as stated before (compound Nos. 5, 11, 22, 31, 37, 42 and 48) can be prepared by catalytically reducing the corresponding unsaturated compound in the presence of a catalyst, such as palladium carbon, Raney nickel and the like, which are conventionally used for the catalytic reduction reaction.

The compound (I) according to this invention exhibits an excellent effect on the treatment of the peptic ulcers. This fact is proved by the following pharmacological experiments. In these experiments, there was used Gefarnate having analogous structure with the compound according to this invention as the control compound.

Pharmacological experiment

Compounds to be tested (hereinafter refer to test compounds)

6,10,14-trimethyl-5,9,13-octadecatriene-2-on (hereinafter refer to the subject compound A)

6,10,14,18-tetramethyl-5,9,13,17-nonadecatetraene-2-on (hereinafter refer to the subject compound B)

2,7,11,15,19-pentamethyl-6,10,14,18-eicosatetraene-3-on (hereinafter refer to the subject compound C)

6,10,14,18-tetramethyl-5-nonadecaene-2-on (hereinafter refer to the subject compound D)

6,10,14,18-tetramethyl-nonadecane-2-on (hereinafter refer to the subject compound E)

8,12,16,20-tetramethyl-7,11,15,19-heneicosatetraene-4-on (hereinafter refer to the subject compound F)

3-acetyl-6,10,14,18-tetramethyl-5,9,13,17-nonadecatetraene-2-on (hereinafter refer to the subject compound G)

Gefarnate (hereinafter refer to the control compound A)

Pharmacological experiment 1

Effect on the cold and restraint stress ulcer

Method

Preventive effect of the test compounds on the development of the cold and restraint stress ulcer was estimated according to Levine's method [Proc. Soc. Exptl. Biol. Med., 124, 1221 (1967)], using SD strain female rats weighing about 170 g, and being 8–10 weeks old, as test animals.

All test compounds were suspended in 5% gum arabic solution and one drop of Tween 80, and the suspension was orally administered to rat. A dose amounted to 200 mg/kg, and the volume of the administrative dose was controlled to 0.5 ml/100 g B. W. As a blank test, 5% gum arabic solution was administered.

The administration of the test compounds and the blank test were carried out 30 minutes before adopting the cold and restraint stress.

The effect of the test compounds was estimated by finding the value (ulcer index) of the total length of the erosion observed in the glandular portion of the test animals two hours after the cold and restraint stress, and calculating the effect of the administration of said compounds as the inhibition rate of the development of the ulcer from the value.

$$\text{Inhibition rate (\%)} = \frac{\left[\begin{array}{c}\text{Ulcer index}\\\text{of the blank}\\\text{test}\end{array}\right] \text{minus} \left[\begin{array}{c}\text{Ulcer index}\\\text{of the test}\\\text{compound}\end{array}\right]}{\text{Ulcer index of the blank test}} \times 100$$

Results

The inhibition rates of the test compounds to the development of ulcer due to the cold and restraint stress are listed in the following Table a.

Table a

Inhibition rate to the development of the cold and restraint stress ulcer

| Test compounds | Inhibition rate (%) |
| --- | --- |
| The subject compound A | 71.4 |
| The subject compound B | 75.7 |
| The subject compound C | 67.1 |
| The subject compound D | 72.0 |
| The subject compound E | 67.8 |
| The subject compound F | 69.5 |
| The subject compound G | 70.5 |
| The control compound A | 47.2 |

The inhibition rates of the compounds A, B, C, D, E, F and G according to this invention to the development of the ulcer are all higher than that of the control compound A. The subject compound B is particularly the most effective compound.

Pharmacological experiment 2

Effect on subacute aspirin ulcer

Method

Aspirin in amount of 200 mg/kg/day was orally administered to SD strain male rats (body weight of about 250 g, nine weeks old) after abstinence from the food for 24 hours. The rats were fed for one hour, after one hour from said administration, and again abstained from the food. The administration of aspirin was continued for five days in the same schedule as mentioned above. The effect was estimated on the sixth day.

All the test compounds were emulsified with 5% gum arabic solution and one drop of Tween 80. The emulsions were administered continuously for five days, together with aspirin to rat. The dose amounted to 200 mg/kg/day, and the volume of the dose was controlled to 0.5 ml/100 g B. W. The blank test was similarly effected as pharmacological experiment 1.

The effect of the test compound was estimated by finding the value (ulcer index) of the total lengths of erosions developed in the glandular portion of the test animal with respect to the test compounds group and the blank test group, respectively, and calculating from said value the effect of the administration of the test compounds as the inhibition rate.

Results

The inhibition rates of the test compounds to the development of the subacute aspirin ulcer are shown in the following Table b.

Table b

| Test compounds | Inhibition rate to the development of the subacute aspirin ulcer Inhibition rate (%) |
| --- | --- |
| The subject compound A | 56.7 |
| The subject compound B | 73.2 |
| The subject compound C | 50.9 |
| The subject compound D | 61.8 |
| The subject compound E | 48.5 |
| The subject compound F | 52.7 |
| The subject compound G | 64.5 |
| The control compound A | 21.0 |

Inhibitory effect was shown by the subject compounds B and D.

Pharmacological experiment 3

Effect on the Histamine ulcer

Method

According to the Okabe et al. method [Japanese Pharmacopoeia 26 (1) 89–93 (1975)], the inhibitory effects of the test compounds on the development of ulcer due to the administration of histamine were estimated using SD strain male rats weighing about 350 g as the test animals.

The methods for administration and estimation of the effect of the test compounds are carried out according to the procedure in pharmacological experiment 1.

A dose of the test compounds amounted to 100 mg/kg.

The histamine was administered intraperitoneally to the test animal in an amount of 200 mg/kg as the hydrochloride.

The effect was estimated 4 hours after the administration of the histamine.

Results

The inhibition rate of the test compounds on the development of the histamine ulcer are shown in the following Table c.

Table c

| Test compound | Inhibition rate to the development of the histamine ulcer Inhibition rate (%) |
| --- | --- |
| The subject compound A | 50.4 |
| The subject compound B | 53.8 |
| The subject compound C | 44.7 |
| The subject compound D | 35.2 |
| The subject compound E | 22.4 |
| The subject compound F | 49.0 |
| The subject compound G | 40.8 |

Table c-continued

| Test compound | Inhibition rate to the development of the histamine ulcer Inhibition rate (%) |
| --- | --- |
| The control compound A | 15.4 |

The control compound A had no appreciable effect on the histamine ulcer of rat. On the other hand, the subject compounds, particularly B, A and F, exhibited more inhibitory effect than that of the control compound.

Pharmacological experiment 4

Effect on Indomethacin ulcer

Method

The inhibitory effects of the test compounds on the development of the ulcer due to the administration of indomethacin were estimated using SD strain female rats weighing about 200 g as the test animals.

The methods for administration and estimation of the effect of the test compounds are carried out according to the procedure in pharmacological experiment 2.

The dose of the test compound amounted to 100 mg/kg. The indomethacin was orally administered in the dose of 20 mg/kg. The effect was estimated four hours after the administration of indomethacin.

Results

The inhibition rate of the test compounds on the development of the indomethacin ulcer are shown in the following Table d.

Table d

| Test compound | Inhibition rate on the development of indomethacin ulcer Inhibition rate (%) |
| --- | --- |
| The subject compound A | 75.4 |
| The subject compound B | 91.3 |
| The subject compound C | 86.7 |
| The subject compound D | 75.5 |
| The subject compound E | 71.1 |
| The subject compound F | 88.5 |
| The subject compound G | 64.9 |
| The control compound A | 45.0 |

Particularly high inhibitory effect on the development of the ulcer were observed in the cases of the subject compounds B, F and C.

It is concluded that the inhibitory effect of the subject compounds on the development of the ulcer is always higher than that of the control compound.

Pharmacological experiment 5

Toxicity

Method

Test animals, male and female rats of SD strain weighing about 200 g were orally dosed with the test compound in amount of 500–100,000 mg/kg according to the procedure of pharmacological experiment 1.

Result

No side or secondary effect of said compounds was observed at the above dose levels.

From the results of the above-described pharmacological experiments, it was found that the compound (I) according to the invention typically represented by the subject compounds A, B, C, D, E, F and G exhibit a high therapeutic effect on the peptic ulcers, and said effect is superior to the effect of the Gefarnate which has analogous structure with that of the compound of the present invention. Therefore, the compound (I) according to this invention is effective as a therapeutic preparation for the peptic ulcers, for example, to treat and prevent the gastric ulcer, the duodenum ulcer and the like.

The compound according to this invention can be administered orally in a form of powder, tablet, granule, capsule, pill and liquid, and parenterally in injection, suppository and the like. The dose amounts of 50-2000 mg a day when used to treat an adult. It is desirable that the dose varies properly depending upon the symptoms and the administration is divided by proper intervals.

The compound according to this invention can be prepared for administration by any conventional process for pharmaceutical preparation. Therefore, this invention provides the pharmaceutical preparations suitable for a medicine for the human body, which comprises at least one of the compounds according to this invention. Such preparations are provided to be administered by a conventional method with any required carrier or excipient for the production of medidine.

This preparation is desirably provided in a suitable form for absorption from the alimentary canal. The tablet and capsule for oral administration are a form of unit dose, and may contain conventional excipients such as a binder, for example, syrup, gum arabic, gelatine, sorbite, tragacanth gum or polyvinyl pyrolidone; a constituent, for example, lactose, corn starch, calcium phosphate, sorbite of glycine; a lubricant, for example, magnesium stearate, talc, polyethylene glycol or silica; a disintegrator, for example, potato starch; and an acceptable wetting agent, for example, sodium lauryl sulfate. The tablet may be coated by a well-known method in the art. The liquid preparations for oral administration may be an aqueous or oily suspension, solution, syrup, elixir and the like. Alternatively, they may be a dry product which is re-dissolved in water or other suitable vehicle prior to use. Such liquid preparations may contain conventional additives, for example, a suspending agent, such as sorbite syrup, methyl cellulose, glucose/-sugar syrup, gelatine, hydroxyethyl cellulose, carboxymethyl cellulose, aluminium stearate gel and hydrogenated edible fat; an emulsifier such as lecithine, sorbitane mono-oleate and gum arabic; a nonaqueous vehicle such as almond oil, fractionated coconut oil, oiliness ester, propylene glycol and ethyl alcohol; an antiseptics such as methyl p-hydroxy benzoate, propyl p-hydroxybenzoate and sorbic acid.

The preparation for injection are provided in a unit-dose ampoule or vial with an additive antiseptics. The preparations may be a form of suspension, solution or emulsion in an oily or aqueous vehicle, and also may contain a formulating agent such as a suspension agent, stabilizer and/or dispersant. On the other hand, the active ingredient may be a form of powder which is re-dissolved in a suitable vehicle, for example, sterilized water free from exothermic materials, prior to use.

The following examples are merely illustrative and are not presented as a definition of the limit of the present invention. Percentages are by weight unless otherwise specified.

EXAMPLE 1

Synthesis of 6,10,14-trimethyl-5,13-pentadecadiene-2-on

To an ethanol solution of sodium ethylate prepared from 50 ml of ethanol and 2.3 g of metallic sodium, 13 g of ethyl acetoacetate were added dropwise with cooling at a temperature less than 5° C. for 20 minutes. To the resulting solution, a solution containing 20 g of 3,7,11-trimethyl-2,10-dodecadiene-1-bromide in 30 ml of dioxane was then added dropwise for one hour. After the addition was over, the solution was stirred at room temperature for 6 hours, to complete the reaction. After the reaction was over, 50 ml of 10% aqueous sodium hydroxide solution were added dropwise with heating at 50° C. for 10 minutes, and the whole was heated under reflux with stirring for 5 hours. After the reaction was over, the reaction mixture was poured into 300 ml of ice water, and extracted with 200 ml of n-hexane. The extracted layer was washed with water, and dried over $Na_2SO_4$. The solvent was then distilled off under reduced pressure, to obtain 18 g of oily product.

The whole product was subjected to a column chromatography using 300 g of silica gel for column chromatography in size of 60-80 mesh with benzen as an eluate. Fraction, in amount of 14 g, was obtained as an oily product. This fraction exhibited a monospot on a thin layer chromatogram. Boiling point of the product was 122°-124° C./0.5 mmHg.

Elementary analysis of the product having a presumed formula $C_{18}H_{32}O$ gave:

|  | C | H |
|---|---|---|
| Calculated (%) | 81.75 | 12.20 |
| Found (%) | 81.62 | 12.31 |

Found of the mass spectrum—M+264,
Found of the infrared spectrum—(cm$^{-1}$),
$\nu$C—H: 2965, 2930, 2870,
$\nu$C=O: 1718.

EXAMPLE 2

Synthesis of 3,6,10,14,18-pentamethyl-5,9,13,17-nonadecatetraene-2-on

Ethyl 2-methylacetoacetate and geranyl geranylbromide were reacted each other and treated according to the preceding Example 1, except that the crude product was purified by distillation under reduced pressure in place of the column chromatography method, to obtain a fraction having the boiling point of 177°-180° C./0.9 mmHg as the objective product.

Elementary analysis of the product having a presumed formula $C_{24}H_{20}O$ gave:

|  | C | H |
|---|---|---|
| Calculated (%) | 83.65 | 11.70 |
| Found (%) | 83.51 | 11.58 |

Found of the mass spectrum—M+344

EXAMPLE 3

Synthesis of 3-acetyl-6,10,14,18-tetra-methyl-5,9,13,17-nonadecatetraene-2-on

Ethyl isopropinyl acetoacetate and phytyl halide were reacted each other and treated according to the procedure of Example 1, except that 50% oil dispersion of sodium hydride was used in place of sodium ethylate as the condensation agent. There was obtained the objective compound as an oily product having the boiling point of 172°–175° C./1 mmHg.

Elementary analysis of the product having a presumed formula $C_{25}H_{48}O$ gave:

|  | C | H |
|---|---|---|
| Calculated (%) | 82.34 | 13.27 |
| Found (%) | 82.19 | 13.31 |

Found of the mass spectrum—$M^+ 364$,
Found of the infrared spectrum—$(cm^{-1})$,
$\nu C = O$: 1715.

EXAMPLE 4

Synthesis of 3-acetyl-6,10,14,18-tetramethyl-5,9,13,17-nonadecatetraene-2-on

To an ethanol solution of sodium ethylate prepared from 100 ml of ethanol and 4.6 g of metallic sodium, 20 g of acetylacetone were added dropwise with cooling at a temperature less than 10° C. for 30 minutes. 24 Grams of geranylgeranyl bromide were then added dropwise for one hour. After the addition was over, the solution was stirred at room temperature for 5 hours to complete the reaction. The reaction mixture was then poured into 500 ml of ice water, and extracted with 500 ml of n-hexane. The layer of extract was washed with water, and dried over $Na_2SO_4$. The solvent was distilled off under reduced pressure, to obtain 24 g of syrupy product. The whole of the syrupy product was diluted with 30 ml of n-hexane, and the mixture was subjected to the column chromatography using 300 g of silica gel for column chromatography in size of 60–80 mesh, with benzen as the eluent solvent. Fraction, in amount of 18 g, was obtained as oily product which exhibits a monospot on the thin layer chromatogram.

Elementary analysis of the product having a presumed formula $C_{25}H_{40}O_2$ gave:

|  | C | H |
|---|---|---|
| Calculated (%) | 80.59 | 10.82 |
| Found (%) | 80.34 | 10.91 |

Found of the mass spectrum—$M^+ 372$,
Found of the infrared spectrum—$(cm^{-1})$,
$\nu C-H$: 2970, 2930, 2870,
$\delta CH_3$: 1360, 1380,
$\nu C = O$: 1720, 1700.

EXAMPLE 5

Synthesis of 3-acetyl-6,10,14-trimethyl-pentadecane-2-on

10 Grams of 3-acetyl-6,10,14-trimethyl-5,9,13-pentadecatriene-2-on (Compound No. 2 in the Table) were dissolved in 10 g of dioxane, and one gram of 5% palladium-carbon was added to the solution. The mixture was catalytically reduced in hydrogen flow at an ordinary temperature under atmospheric pressure. After the reaction was completed, the palladium-carbon was filtered off, and the filtrate was subjected to distillation under the reduced pressure, to obtain 10 g of oily product. The product was purified by the column chromatography method as described in Example 1.

Elementary analysis of the product having a presumed formula $C_{20}H_{38}O_2$ gave:

|  | C | H |
|---|---|---|
| Calculated (%) | 77.36 | 12.34 |
| Found (%) | 77.29 | 12.27 |

Found of the mass spectrum—$M^+ 310$,
Found of the IR spectrum—$(cm^{-1})$,
$\nu C = O$: 1718, 1700.

EXAMPLE 6

Synthesis of 7,11,15,19-tetramethyl-eicosane-3-on

The reaction and treatments of 7,11,15,19-tetramethyl-6,10,18-eicosatriene-3-on were carried out according to the procedure in Example 5. There was thus obtained oily product having the boiling point of 180°–183° C./3 mmHg as the objective compound.

Elementary analysis of the product having a presumed formula $C_{24}H_{48}O$ gave:

|  | C | H |
|---|---|---|
| Calculated (%) | 81.74 | 13.72 |
| Found (%) | 81.64 | 13.81 |

Found of the mass spectrum—$M^+ 352$.

EXAMPLE 7

| 6,10,14,18-tetramethyl-5,9,13,17-nonadecatetraene-2-on | 5 g |
|---|---|
| Microcrystallized cellulose | 80 g |
| Corn starch | 20 g |
| Lactose | 22 g |
| Polyvinyl pyrolidone | 3 g |
| Total | 130 g |

The above ingredients were granulated by a conventional process, and then filled into 500 hard capsules of gelatine. These capsules contained the active ingredient in amount of 10 mg per capsule.

EXAMPLE 8

Powder

| 6,10,14,18-tetramethyl-5,9,13,17-nonadecatetraene-2-on | 50 g |
|---|---|
| Microcrystallized cellulose | 400 g |
| Corn starch | 550 g |
| Total | 1,000 g |

The active ingredient was dissolved in acetone, and the resulting solution was absorbed to the microcrystallized cellulose, followed by dryness. The product was mixed with the corn starch to make powder, that is, powdery preparation having 20 trituration of the active ingredient, by conventional process.

EXAMPLE 9

Tablet

| | |
|---|---|
| 6,10,14,18-tetramethyl-5,9,13,17-nonadecatetraene-2-on | 5 g |
| Corn starch | 10 g |
| Purified white sugar | 20 g |
| Carboxymethylcellulose calcium | 10 g |
| Microcrystallized cellulose | 40 g |
| Polyvinyl pyrolidone | 5 g |
| Talc | 10 g |
| Total | 100 g |

The active ingredient was dissolved in acetone, and the solution was adsorbed to the microcrystallized cellulose, followed by dryness. This product was mixed altogether with the corn starch, the purified white sugar and the carboxymethyl cellulose calcium. The aqueous polyvinyl pyrolidone solution was added to said mixture, as the binder. This product was granulated by conventional process. The granules were mixed with talc as a lubricant, and the mixture was then processed to form the tablets weighing 200 mg per tablet. The tablets contained 10 mg of the active ingredient per tablet.

EXAMPLE 10

Injection

| | |
|---|---|
| 6,10,14,18-tetramethyl-5,9,13,17-nonadecatetraene-2-on | 10 g |
| Nikkol HCO-60 | 37 g |
| Sesame oil | 2 g |
| Sodium chloride | 9 g |
| Propylene glycol | 40 g |
| Phosphate buffer solution (0.1 M, pH 6.0) | 100 ml |

Distilled water in amount to make the total volume of 1,000 ml

The active ingredient, the Nikkol HCO-60, the sesame oil and half amount of the propylene glycol were mixed altogether, and heated at about 80° C. to dissolve them. This mixture was added the distilled water at about 80° C. in which the phosphate buffer solution, the sodium chloride and the propylene glycol were previously dissolved, to make the aqueous solution in total volume of 1,000 ml. This aqueous solution was dividually charged into 2 ml ampoules. The ampoules were fused to seal, and heated to sterilize. The ampoules contained the active ingredient in amount of 20 mg per ampoule.

What is claimed is:

1. A method of treating a peptic ulcer which comprises administering to a patient an effective ulcer treating amount of an aliphatic ketone derivative of the general formula:

$$R_3-CH_2-\underset{\underset{H}{|}}{\overset{\overset{CH_3}{|}}{C}}=\underset{}{C}-CH_2-\underset{\underset{H}{|}}{\overset{\overset{R_2}{|}}{C}}-\underset{}{\overset{\overset{R_1}{|}}{C}}=O$$

wherein $=$ represents a saturated or unsaturated bond,
  $R_1$ is hydrogen or a lower alkyl group,
  $R_2$ is a hydrogen atom, a lower alkyl group, or a lower alkylcarbonyl group,
  $R_3$ is an aliphatic hydrocarbon group of the formula:

$$H-(CH_2-\underset{\underset{f}{|}}{\overset{\overset{CH_3}{|}}{C}}-\underset{\underset{e}{|}}{\overset{\overset{H}{|}}{C}}-CH_2)_m(-CH_2-\underset{\underset{d}{|}}{\overset{\overset{CH_3}{|}}{C}}-$$

$$-\underset{\underset{c}{|}}{\overset{\overset{H}{|}}{C}}-CH_2)_m(-CH_2-\underset{\underset{b}{|}}{\overset{\overset{CH_3}{|}}{C}}-\underset{\underset{a}{|}}{\overset{\overset{H}{|}}{C}}-CH_2)_l$$

wherein l, m and n are 0 or 1, provided that $l+m+n \geq 2$; and a, b, c, d, e and f are hydrogen atoms, or they may form a bond of a-b, c-d, e-f, provided that if the bond $=$ is a saturated bond, the a, b, c, d, e and f all represent hydrogen atoms.

2. A method according to claim 1, wherein the aliphatic ketone derivative is administered to the patient in a dosage of 50–2000 mg a day.

* * * * *